(12) United States Patent
Kostner et al.

(10) Patent No.: US 10,508,941 B2
(45) Date of Patent: Dec. 17, 2019

(54) FLOW SENSOR

(71) Applicant: Sensirion AG, Staefa ZH (CH)

(72) Inventors: Stefan Kostner, Staefa ZH (CH);
Thomas Kiefer, Staefa ZH (CH);
Lukas Mahler, Staefa ZH (CH)

(73) Assignee: SENSIRION AG, Staefa ZH (CH)

( * ) Notice: Subject to any disclaimer, the term of this patent is extended or adjusted under 35 U.S.C. 154(b) by 239 days.

(21) Appl. No.: 15/390,756

(22) Filed: Dec. 27, 2016

(65) Prior Publication Data

US 2017/0184433 A1     Jun. 29, 2017

(30) Foreign Application Priority Data

Dec. 28, 2015   (EP) .................................... 15202841

(51) Int. Cl.
| | | |
|---|---|---|
| *G01F 1/688* | (2006.01) | |
| *G01F 1/696* | (2006.01) | |
| *G01P 5/10* | (2006.01) | |
| *G01F 1/684* | (2006.01) | |
| *A61B 5/026* | (2006.01) | |

(52) U.S. Cl.
CPC ............ *G01F 1/6888* (2013.01); *A61B 5/026* (2013.01); *G01F 1/6842* (2013.01); *G01F 1/6845* (2013.01); *G01F 1/696* (2013.01); *G01P 5/10* (2013.01)

(58) Field of Classification Search
CPC .... G01F 1/6888; G01F 1/6845; G01F 1/6842; G01F 1/696; G01P 5/10; A61B 5/026
See application file for complete search history.

(56) References Cited

U.S. PATENT DOCUMENTS

| | | | |
|---|---|---|---|
| 6,527,835 B1 | 3/2003 | Manginell | |
| 7,255,001 B1* | 8/2007 | Davis | G01F 1/6845 |
| | | | 73/204.26 |
| 2004/0113267 A1* | 6/2004 | Yogo | G01F 1/6842 |
| | | | 257/723 |
| 2008/0210001 A1 | 9/2008 | Kanne | |
| 2010/0139389 A1* | 6/2010 | Morita | G01F 1/6845 |
| | | | 73/204.11 |
| 2012/0290268 A1* | 11/2012 | Bey | G01D 11/245 |
| | | | 702/189 |
| 2013/0160540 A1* | 6/2013 | Okano | G01F 1/684 |
| | | | 73/202.5 |

FOREIGN PATENT DOCUMENTS

| | | |
|---|---|---|
| EP | 1 024 350 | 8/2000 |
| EP | 1 873 499 | 1/2008 |
| EP | 2469270 | 6/2012 |
| JP | 2007212197 | 8/2007 |
| JP | 2012141181 | 7/2012 |
| WO | 2013/070791 | 5/2013 |

* cited by examiner

*Primary Examiner* — Justin Seo
*Assistant Examiner* — John M Royston
(74) *Attorney, Agent, or Firm* — JMB Davis Ben-David

(57) ABSTRACT

The invention relates to a flow sensor (1), comprising: a semiconductor module (2) on which a temperature sensing means (13a, 13b) and a heat source (12) are arranged, a flow channel (6) for guiding the fluid medium in a flow direction (D), and a wall (W) delimiting the flow channel, wherein said heat source (12) and said temperature sensing means (13a, 13b) are configured such that they are in thermal contact with said wall (W). According to the invention, said wall (W) comprises a glass member (4) and a metal member (3a), wherein the glass member (4) is connected to the metal member (3a).

14 Claims, 2 Drawing Sheets

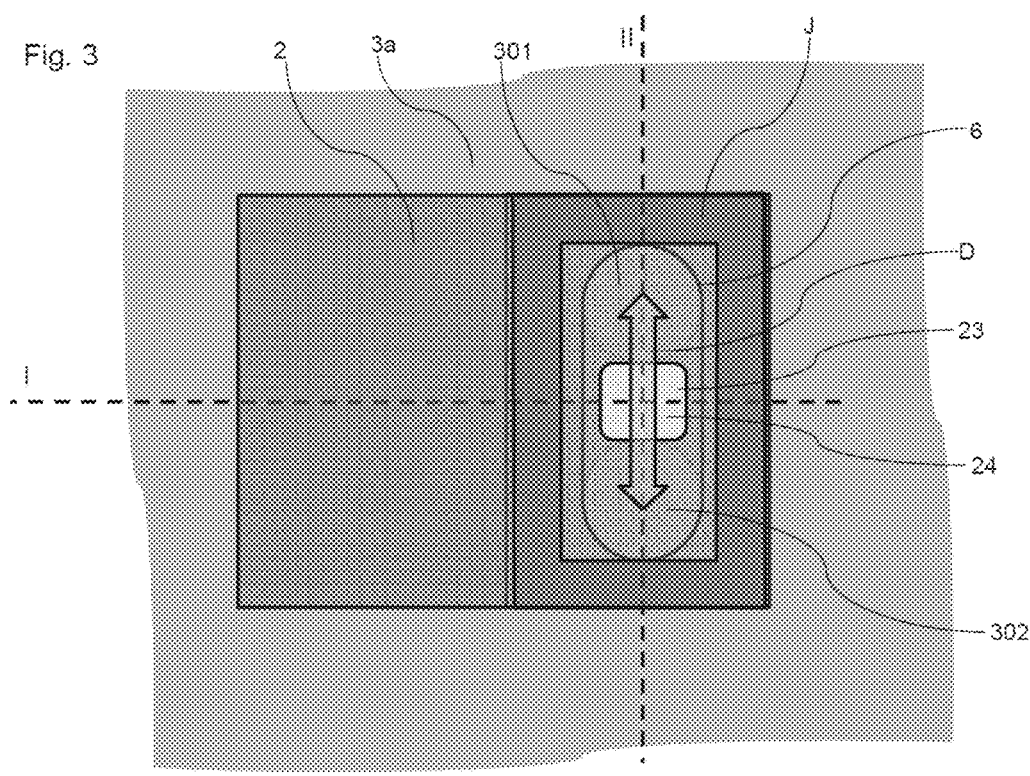
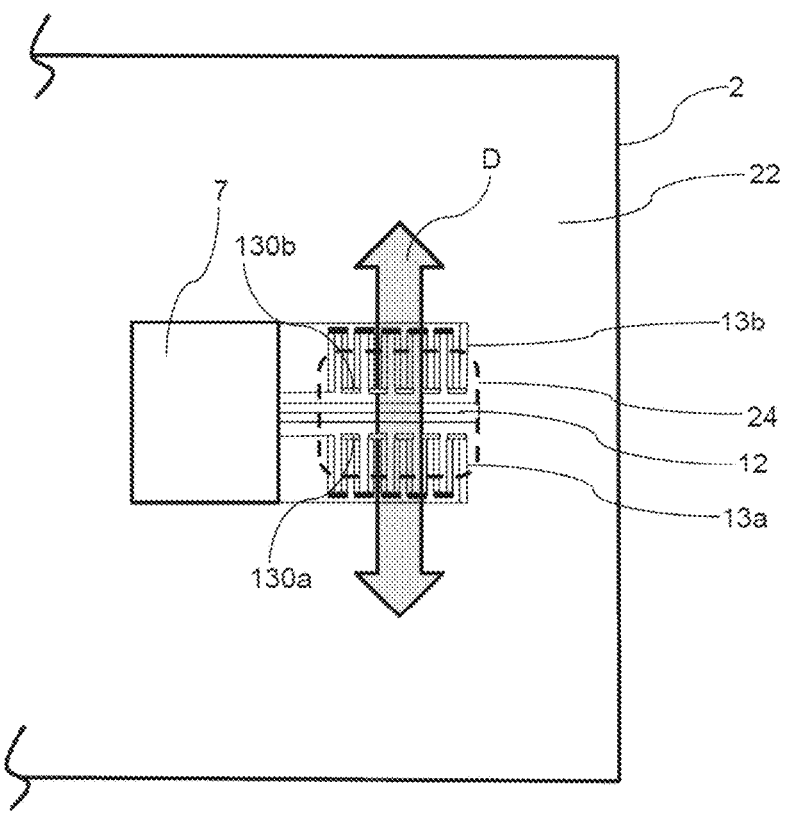

FLOW SENSOR

CROSS REFERENCE TO RELATED APPLICATIONS

Benefit is claimed to European Patent Application No. EP15202841.1, filed on Dec. 28, 2015, the contents of which are incorporated by reference in their entirety.

FIELD

The invention relates to a flow sensor, particularly for measuring the flow velocity, mass flow rate, and/or volumetric flow rate of a fluid medium (e.g. a gas, liquid or mixture of a gas and a liquid).

BACKGROUND

It is known in the state-of-the-art to measure the flow velocity or the mass or volumetric flow rate of a liquid or gaseous medium by means of a semiconductor module on which a thermal source and a suitable temperature sensing means are arranged. The flow leads to a change in the temperature distribution of the thermal source which can be measured using the temperature sensing means.

However, semiconductor modules of this kind are very sensitive. When in contact with certain liquids or gases, such modules can be easily contaminated or damaged. Furthermore, mechanical loads may damage the module. In some applications, the problem may further arise, that the medium that is to be measured can be contaminated by the semiconductor module. Therefore, the semiconductor modules have to be separated from the medium by means of protective layers, for instance, which is difficult to achieve however.

Particularly in cases where the flow sensor is to be arranged inside the body of a body of a patient further precautions have to be taken to assure that the sensor and its materials do not pose a risk for the patient.

SUMMARY

Therefore, based on the above, the problem underlying the present invention is to provide a flow sensor of the aforementioned kind that reliably shields the components of the flow sensor from the medium to be measured and can particularly be used as a medical device or part of such a device that is in contact with a patient, particularly body fluids of the patient.

This problem is solved by a flow sensor having the features of claim 1.

BRIEF DESCRIPTION OF THE DRAWINGS

Further embodiments, features and advantages of the present invention will be described below with reference to the Figures, wherein:

FIG. 3 shows a top view of the flow sensor according to FIGS. 1 and 2; and

FIG. 4 shows a plan view of the second side of the semiconductor module and the heat source and temperature sensing means arranged thereon.

DETAILED DESCRIPTION

Figure 1:
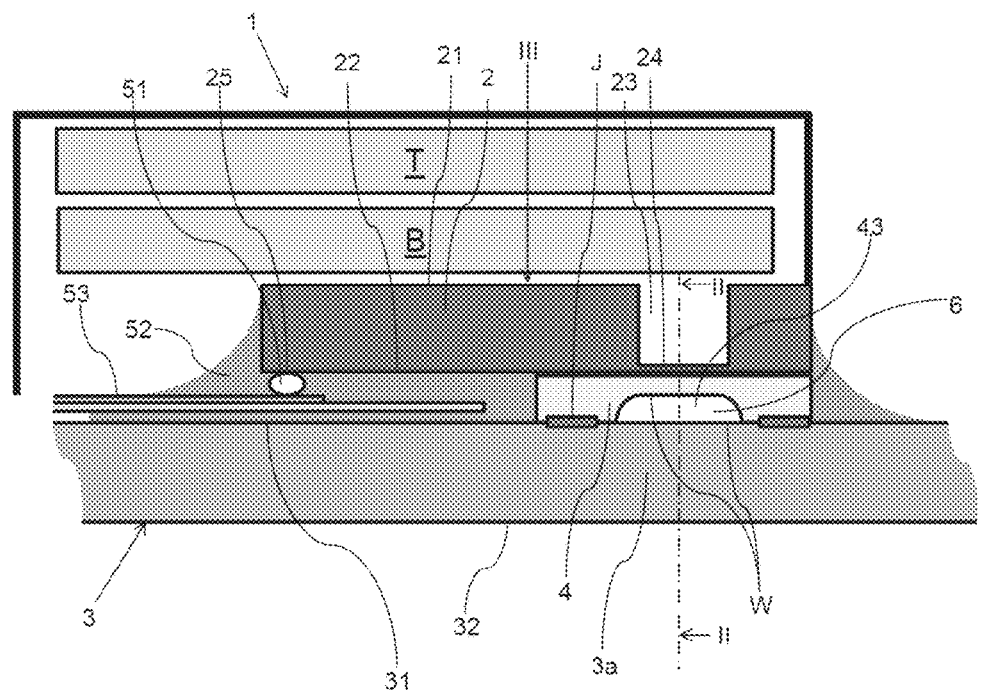
FIG. 1 shows a cross sectional view of a flow sensor according to the invention across the flow channel of the sensor.
Figure 2:
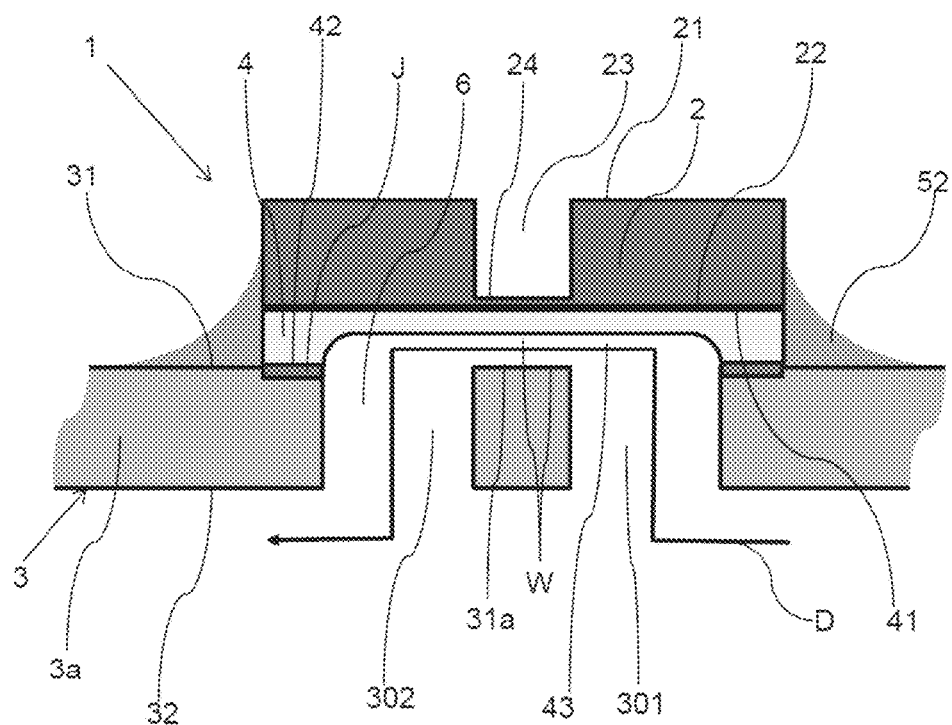
FIG. 2 shows a further cross sectional view along the flow channel.

According to claim 1, a flow sensor for measuring the fluid flow, particularly the volumetric flow or mass flow of a fluid medium is proposed, comprising:
- a semiconductor module on which a temperature sensing means and a heat source are arranged,
- a flow channel for guiding the fluid medium in a flow direction, and
- a wall delimiting the flow channel, wherein said heat source and said temperature sensing means are configured such that they are in thermal contact with said wall and therefore with said medium when the medium flows through the flow channel in said flow direction.

According to the invention said wall comprises or is formed by a glass member and a metal member, wherein the glass member is connected to the metal member, namely particularly such that said flow channel is formed.

According to an embodiment, the metal member is made of a metal or at least comprises a metal, wherein particularly said metal is titanium or a steel. Preferably, said steel is a stainless steel, particularly a surgical stainless steel.

In other words, the glass member is connected to the metal member at a defined junction (see also below) either directly or via an intermediate material, preferably via at least one of: an adhesive bond (also known as substance-to-substance bond or material connection), which may form a seamless connection between the two members, a force-locked connection, a positive connection.

Particularly, in respective embodiments of the present invention, said connection may be achieved by gluing, welding, particularly plasma or laser welding, or soldering.

Particularly, in case the connection is achieved by means of soldering, the glass member preferably comprises a metallized area (e.g. on its first side, see below) containing Gold (Au), which area may be e.g. 2000 nm thick and may be obtained by means of sputtering. This area may then be soldered to the metal member using e.g. a SnInAg alloy (e.g. Sn77.25 In20 Ag2.8, melting temperature 184° C.) as a solder by forming (as said junction) a brazing ring having a thickness of e.g. 50 µm.

Particularly, according an embodiment of the present invention, the glass member is connected to the metal member by means of laser welding using a laser, wherein the glass member is transparent or at least substantially transparent to the light emitted by said laser, wherein a transmissivity change is generated at an interface (e.g. at said junction) between the glass member and the metal member, and wherein the glass member is irradiated with said light emitted by said laser creating a localized high temperature at the interface (e.g. said junction) from energy supplied by the laser, and wherein the glass member and the metal member are softened adjacent said interface with diffusion across the interface to fuse the glass member and the metal member. According to an embodiment, said transmissivity change is accomplished with the difference in transmissivity between the glass member and the metal member and/or by depositing a blocking heat absorption coating on at least a portion (e.g. at said junction) of a surface of the glass member or of the metal member at the mating interface. Here, the step of generating a localized high temperature at the interface (e.g. said junction) may include generating a plasma from the heat absorption coating and high temperature plasma; and the step of softening the glass member and the metal member adjacent the interface with diffusion across the interface may include diffusing the heat absorption coating plasma into the glass member and the metal member. Details of the afore-described laser welding process are e.g. described in WO2013/070791 A1.

Further, according to an embodiment of the present invention, the glass member is arranged between the semiconductor module and the metal member.

Furthermore, according to an embodiment of the present invention, the metal member comprises two neighbouring through holes each extending from a first side of the metal member to a second side of the metal member, wherein one of said through holes forms an inlet and the other one forms an outlet of said flow channel. Particularly, said first and said second side of the metal member extend parallel with respect to each other and form flat surfaces, respectively.

Further, according to an embodiment of the present invention, the glass member is connected to the metal member at a defined junction, wherein said junction extends circumferentially on the first side of the metal member around said two through holes, and may comprise, for example, a rectangular and flat shape.

Further, according to an embodiment of the present invention, the glass member comprises a first, particularly flat side, facing said semiconductor module and a second side facing the first side of the metal member, wherein the second side of the glass member is connected to the first side of the metal member (namely via said junction) such that a recess present in the second side of the glass member is fluidly connected to said through holes, so that said flow channel extends from one through hole (forming said inlet off the flow channel) via the recess of the glass member to the other through hole (forming said outlet of the flow channel). Alternatively (or in addition), said recess may be formed in the first side of the metal member (e.g. between the two through holes).

Further, according to an embodiment of the present invention, the semiconductor module comprises a first side facing away from the glass member and a second side facing the first side of the glass member, wherein the semiconductor module comprises a recess in its first side which comprises a bottom (that particularly forms a membrane), which bottom forms a region of said second side of the semiconductor module. The bottom or membrane may comprise a thickness in the range from 1 μm to 10 μm.

Further, according to an embodiment of the present invention, said heat source and said temperature sensing means are at least partially arranged on said bottom on the second side of the semiconductor module which may form a component side of the semiconductor module, so that the heat source and said temperature sensing means are in thermal contact with the glass member. Here, particularly, the heat source and the temperature sensing means can contact the glass member (namely its first side) directly or via an intermediate layer of another material (e.g. an adhesive).

Furthermore, according to a preferred embodiment of the present invention, said bottom of the recess of the semiconductor module is arranged above the flow channel, such that the bottom faces a region of the first side of the metal member, which region is arranged between the two through holes of the metal member.

Further, in an embodiment of the present invention, the temperature sensing means comprises two temperature sensors, wherein, with respect to said flow direction, one temperature sensor is arranged upstream said heat source and the other temperature sensor is arranged downstream said heat source so that the heat source is arranged between the two temperature sensors.

Particularly, the heat source is configured to generate a temperature distribution in said glass member, wherein due to the flow of the medium in the flow channel in the flow direction, said temperature distribution becomes asymmetric which is reflected in the temperatures measured by means of the two temperature sensors. These temperatures are thus indicative of the flow velocity of the fluid medium in the flow channel.

Furthermore, particularly, the flow sensor comprises an analyzing circuit arranged on the semiconductor module which analyzing circuit is configured to determine one of the flow velocity, the mass flow rate, the volumetric flow rate of the medium in the flow channel using said temperatures measured by the two temperature sensors in a known manner (see also below).

According to a further embodiment of the present invention, the semiconductor module is connected to the metal member by means of an adhesive (e.g. epoxy).

Further, according to an embodiment of the present invention, the flow sensor comprises a housing, wherein said metal member forms at least a part of said housing, particularly a part that is integrally formed with the housing. Alternatively, the metal member may form a separate member that is connected to a separate part forming said housing together with the metal member.

Particularly, the housing is configured to enclose the components of of the flow sensor described herein, particularly in a sealed manner.

According to a further embodiment of the present invention, the semiconductor module comprises electrical contacts on its second side, which electrical contacts are each connected to a flexible conductor via a solder junction for connecting the flow sensor to the outside world. Particularly data measured by the flow sensor such as flow velocities of the medium flowing through the flow channel may be delivered to the outside world (e.g. another component) via said flexible conductor.

Particularly, said solder junctions and at least a section of said flexible conductor are embedded between the semiconductor module and the metal member in said adhesive which connects the semiconductor module to the metal member.

Furthermore, alternatively or in addition to the flexible conductor, the flow sensor may comprise a transmitter for transmitting said data measured by the flow sensor in a wireless fashion to a remote receiver. Such a transmitter, e.g. a radio frequency interface for transmitting the measured data, is for instance disclosed in EP2469270A1.

The flow sensor according to the present invention can be used for measuring flow velocities, mass flow rates, and/or volumetric flow rates of fluids such as body fluids (e.g. urine, blood, drainage in case of a hydrocephalus etc.), an infusion liquid, particularly blood, an aqueous solution, a saline solution, a physiological saline solution, a drug in physiological saline etc.

Further, the flow sensor of the present invention can be formed as a stand-alone device, that is e.g. encapsulated by a titanium cap (e.g. on a catheter hose, wherein said metal member may form said cap or a part thereof), but may also form a part of a larger unit, such as a micro dosage pump.

The basic construction of the flow sensor 1 according to the present invention can be seen from FIGS. 1 to 4 which show an embodiment of the flow sensor 1 according to the present invention.

The flow sensor 1 comprises a semiconductor module 1, which is arranged in a housing 3. The housing 3 preferably encapsulates all components of the flow sensor 1. The flow sensor 1 may be a stand-alone device, but may also form a part of an implant or a medical device such as a catheter or a micro dosing pump (see also above).

The flow sensor 1 is adapted for measuring at least one of the flow velocity, the mass flow rate, and the volumetric flow rate of a fluid medium. To this end, the flow sensor comprises a semiconductor module 2 on which a temperature sensing means 13a, 13b and a heat source 12 are arranged, a flow channel 6 for guiding the fluid medium in a flow direction D, and a wall W surrounding or defining the flow channel 6, wherein said heat source 12 and said temperature sensing means 13a, 13b are configured such that they are in thermal contact with said wall W and therefore with said medium when the medium flows through the flow channel 6 in said flow direction D. According to the invention said wall W comprises or is formed by a glass member (i.e. a member formed out of a glass, e.g. borosilicate, quartz or other suitable materials) 4 and a metal member 3a, wherein the glass member 4 is connected to the metal member 3a at a junction J such that said flow channel 6 is formed. Preferably, the metal member 3a is a titanium member 3a (i.e. is made out of titanium or at least comprises titanium) but may also be formed out of a suitable steel or another suitable metal.

The semiconductor module 2 comprises a first side 21 facing away from the glass member 4 and a second side 22 facing a first side 41 of the glass member 4. Further, the semiconductor module 2 comprises a recess 23 on the first side 21 which comprises thin a bottom 24 that forms a part of said second side 22 of the semiconductor module 2.

The heat source 12 and said temperature sensing means 13a, 13b are at least partially arranged on said bottom 24 on the second side 22 of the semiconductor module 2 (cf. FIG. 4) so that the heat source 12 and said temperature sensing means 13a, 13b are in thermal contact with the glass member 4. The heat source 12 and the temperature sensing means may contact the first side 41 of the glass member 4 directly or via an intermediate layer of another material (e.g. an adhesive).

The glass member 4 further comprises a second side 42 facing a first side 31 of the metal member 3a, wherein the second side 42 of the glass member 4 is connected to the first side 31 of the metal member 3a via said junction J such that a recess 43 of the glass member 4 that is formed on the second side 42 of the glass member 4 is fluidly connected to two through holes 301, 302 (cf. FIG. 2) of the metal member 3a, which holes 301, 302 extend from the first side 31 of the metal member 3a to the second side 32 of the metal member, so that said flow channel 6 extends from one through hole 301 forming an inlet of the flow channel 6 via the recess 43 of the glass member 4 to the other through hole 302 which forms an outlet of the flow channel 6. Due to the fact, that the junction J extends circumferentially around the two through holes (cf. e.g. FIG. 3) the flow channel 6 is sealed by means of the connection between the glass member 4 and the metal member 3a.

Further, the semiconductor module is connected to the metal member 3a by means of an adhesive 52 that fills a gap between the semiconductor module 2 and the metal member 3a.

Further, said bottom 24 of the recess 23 of the semiconductor module 2 is arranged above the flow channel 6 and faces a region 31a of the first side 31 of the metal member 3a that is arranged between the two through holes 301, 302 of the metal member 3a. Hence, the fluid medium passes through the flow channel 6 in the flow direction D along said bottom 24 as indicated in FIG. 4. Due to said recess 23 heat conduction is reduced and the surrounding chip is protected from excessive heat. Further, the necessary energy for the heat source 12 is reduced.

For measuring the flow velocity of the fluid medium or related quantities (see above) the temperature sensing means 13a, 13b comprises two temperature sensors 13a, 13b, wherein with respect to said flow direction D, one temperature sensor 13a is arranged upstream said heat source 12 and the other temperature sensor 13b is arranged downstream said heat source 12 (note that in FIG. 4 both possible flow directions D are indicated).

As indicated in FIG. 4 the heat source 12 and the temperature sensors 13a, 13b may be formed by an integrated circuit that is arranged on the second (component) side 22 of the semiconductor module 2, particularly using a CMOS technique. Here, the heat source 12 may be formed by a resistor. The two temperature sensors 13a, 13b may be formed as thermopiles, respectively.

The heat source 12 is configured to generate a temperature distribution in said glass member 41 that is arranged adjacent said bottom/membrane 24, wherein due to the flow of the medium in the flow channel 6 in the flow direction D said temperature distribution becomes asymmetric which is reflected in the temperatures measured by means of the two temperature sensors 13a, 13b.

Particularly, the heat source 12 and at least the inner contact rows 130a, 130b of the thermopiles 13a, 13b are arranged on the bottom 24 of the recess 23 on the second side 22 of the semiconductor module 2 and are in thermal contact with the glass member 4. They can directly contact the first side 41 of the glass member 4 or can be separated by the glass member 4 by means of a thin layer of thermally conductive material (e.g. an adhesive).

Furthermore, an analyzing circuit 7 is arranged on the semiconductor module 2, which circuit 7 is configured to operate the heat source 12, particularly with a constant current, a constant temperature, a constant voltage, or pulsed. Furthermore, the analyzing circuit 7 is configured to measure the difference Δ of the temperature differences over the thermopiles 13a, 13b. Since the outer contact rows of the thermopiles 13 are essentially on the same temperature level, the difference Δ corresponds essentially to the temperature difference at the inner contact rows 130a. 130b.

As already mentioned, during operation the heat source 12 generates a temperature distribution in the glass member 4 adjacent the flow channel 6. Due to the flow of the medium in the channel 6 this temperature distribution becomes asymmetric so that the difference Δ of the temperature differences provides a measure for the flow velocity. From this value the analyzing circuit 7 derives the suitable measuring value, such as flow velocity, volumetric flow rate, or mass flow rate of the medium.

For connecting the semiconductor module, particularly the analyzing circuit 7, to the outside world (i.e. for transmitting measure data of the medium) the semiconductor module 2 comprises electrical contacts 25 on its second side 22, which electrical contacts 25 are each connected to a flexible conductor 53 via a solder junction 51 (cf. FIG. 1). Particularly, said solder junctions 51 and at least a section of said flexible conductor 53 are embedded between the semiconductor module 2 and the metal member 3a in said adhesive 52 connecting the module 2 to the metal member 3a.

Alternatively or in addition, the flow sensor 1 comprises a transmitter T for transmitting data measured by the flow sensor 1 (e.g. flow velocity, volumetric flow rate, or mass flow rate of the medium) in a wireless fashion to a remote receiver. The transmitter may be arranged in the housing 3 of the flow sensor 1 on top of the semiconductor module 2. Further, alternatively, the transmitter T may be arranged on the flexible conductor 53. Further, a battery B for powering the components of the flow sensor 1 may be arranged in the housing 3 of the flow sensor 1, e.g. on top of the semi-conductor module 2, e.g. between the transmitter T and the semi-conductor module 2. Instead of a battery T or in addition, energy for operating the flow sensor 1 may be coupled into the sensor 1 in a wireless fashion according to an embodiment of the present invention.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A flow sensor, comprising:
   a semiconductor module on which a temperature sensing means and a heat source are arranged,
   a flow channel for guiding the fluid medium in a flow direction, and
   a wall delimiting the flow channel, wherein said heat source and said temperature sensing means are configured such that they are in thermal contact with said wall,
   wherein
   said wall comprises a glass member and a metal member, wherein the glass member is connected to the metal member such that said flow channel is formed, wherein the glass member is arranged between the semiconductor module and the metal member, and wherein the metal member comprises two neighbouring through holes each extending from a first side of the metal member to a second side of the metal member, wherein one of said through holes forms an inlet and the other one forms an outlet of said flow channel.

2. The flow sensor of claim 1, wherein the metal member is made of a metal or at least comprises a metal, wherein particularly said metal is titanium or a steel.

3. The flow sensor according to claim 1, wherein the glass member is connected to the metal member at a defined junction, wherein said junction extends circumferentially on the first side of the metal member around said two through holes.

4. The flow sensor according to claim 1, wherein the glass member comprises a first side facing said semiconductor module and a second side facing the first side of the metal member, wherein the second side of the glass member is connected to the first side of the metal member such that a recess formed in the second side of the glass member or in the first side of the metal member is fluidly connected to said through holes, so that said flow channel extends from one through hole via said recess to the other through hole.

5. The flow sensor according to claim 4, wherein the semiconductor module comprises a first side facing away from the glass member and a second side facing the first side of the glass member, wherein the semiconductor module comprises a recess in its first side which comprises a bottom that forms a part of said second side of the semiconductor module.

6. The flow sensor of claim 5, wherein said heat source and said temperature sensing means are at least partially arranged on said bottom on the second side of the semiconductor module so that the heat source and said temperature sensing means are in thermal contact with the glass member.

7. The flow sensor according to claim 5, wherein said bottom is arranged above the flow channel, such that the bottom faces a region of the first side of the metal member, which region is arranged between the two through holes of the metal member.

8. The flow sensor according to claim 1, wherein the semiconductor module is connected to the metal member by means of an adhesive.

9. The flow sensor according to claim 1, wherein the flow sensor comprises a housing, wherein said metal member forms at least a part of said housing.

10. The flow sensor according to claim 1, wherein the semiconductor module comprises electrical contacts on its second side, which electrical contacts are each connected to a flexible conductor via a solder junction.

11. The flow sensor according to claims 8, wherein solder junctions and at least a section of a flexible conductor are embedded between the semiconductor module and the metal member in said adhesive.

12. The flow sensor according to claims 10, wherein said solder junctions and at least a section of said flexible conductor are embedded between the semiconductor module and the metal member in said adhesive.

13. The flow sensor according to claims 1, wherein the flow sensor comprises a transmitter for transmitting data measured by the flow sensor to a remote receiver.

14. A flow sensor, comprising:
    a semiconductor module on which a temperature sensing means and a heat source are arranged,
    a flow channel for guiding the fluid medium in a flow direction, and
    a wall delimiting the flow channel, wherein said heat source and said temperature sensing means are configured such that they are in thermal contact with said wall,
    wherein said wall comprises a glass member and a metal member, wherein the glass member is connected to the metal member,
    wherein the metal member comprises two neighbouring through holes each extending from a first side of the metal member to a second side of the metal member, wherein one of said through holes forms an inlet and the other one forms an outlet of said flow channel,
    wherein the glass member comprises a first side facing said semiconductor module and a second side facing the first side of the metal member, wherein the second side of the glass member is connected to the first side of the metal member such that a recess formed in the second side of the glass member or in the first side of the metal member is fluidly connected to said through holes, so that said flow channel extends from one through hole via said recess to the other through hole, and
    wherein the semiconductor module comprises a first side facing away from the glass member and a second side facing the first side of the glass member, wherein the semiconductor module comprises a recess in its first side which comprises a bottom that forms a part of said second side of the semiconductor module.

* * * * *